(12) United States Patent
Nigam (10) Patent No.: US 6,543,610 B1
(45) Date of Patent: Apr. 8, 2003

(54) SYSTEM FOR PACKAGING AND HANDLING AN IMPLANT AND METHOD OF USE

(76) Inventor: Alok Nigam, 21381 Birdhollow Dr., Trabuco Canyon, CA (US) 92679

( * ) Notice: Subject to any disclaimer, the term of this patent is extended or adjusted under 35 U.S.C. 154(b) by 0 days.

(21) Appl. No.: 09/660,371

(22) Filed: Sep. 12, 2000

(51) Int. Cl.⁷ .............................................. A45C 11/04
(52) U.S. Cl. ........................................ 206/5.1; 294/1.2
(58) Field of Search ..................... 206/5.1, 205, 210; 294/1.2; 356/246; 606/107; 623/6.11, 6.12–6.51

(56) References Cited

U.S. PATENT DOCUMENTS

| | | | |
|---|---|---|---|
| 3,770,113 A | | 11/1973 | Thomas |
| 4,039,827 A | | 8/1977 | Zdrok et al. |
| 4,392,569 A | * | 7/1983 | Shoup ........................ 206/5.1 |
| 4,545,478 A | | 10/1985 | Waldman |
| 5,071,276 A | * | 12/1991 | Nielsen et al. ............... 206/5.1 |
| 5,941,583 A | | 8/1999 | Raimondi |

* cited by examiner

Primary Examiner—Luan K. Bui
(74) Attorney, Agent, or Firm—Fulbright & Jaworski L.L.P.

(57) ABSTRACT

A system designed to store an implant together with the tools necessary to implant the stored implant, and a method of using said system. Such system includes an implant storage tool adapted to retain the implant within a storage container. The implant storage tool is operable to provide an implant applicator.

23 Claims, 6 Drawing Sheets

SYSTEM FOR PACKAGING AND HANDLING AN IMPLANT AND METHOD OF USE

FIELD OF THE INVENTION

The present invention relates to a system for packaging, handling and applying implants. Additionally, this invention relates to a method for introducing a corneal implant to the corneal surface.

BACKGROUND OF THE INVENTION

Current methods and devices used to store small, delicate, and normally transparent implants entail free-floating the implant in a volume of storage fluid contained within a storage bottle or other container. This manner of storage is oftentimes used to preserve retinal transplants, brain tissue transplants, corneal implants, tissue biopsies and any other delicate biological specimen. Free-floating storage, however, subjects a stored specimen or implant to fluid agitation, which can severely and irreparably damage the integrity of the stored material. In addition, isolating transparent specimens from the storage fluid is difficult to achieve.

Corneal implants are especially susceptible to the above described problem. Corneal implants are used to correct visual disorders such as Myopia or near-sightedness, Hyperopia or far-sightedness, Presbyopia or difficulty in accommodating a change in focus, and Astigmatism. To correct these disorders, the implant is introduced into the body of the cornea in known ways, such as after a flap is formed and an under surface of the cornea is exposed. The implant, changes the shape of the cornea and alters its refractive power. These implants are generally made of various types of hydrogels, but can include other polymers, tissue implants, or the like.

In the past, storing the corneal implant required free-floating the implant in a volume of storage fluid contained within a storage container. To retrieve the implant, one had to first locate the implant within the fluid, and then remove the implant using a filter device or sequestering tool. In the case of a corneal implant, locating the implant is complicated by both the size and transparency of the implant. For instance, a corneal implant generally has a diameter of about 4.0 to 7.0 mm and a center that is normally fabricated having a thickness ranging from 25 to 50 microns. Due this minuscule size, physically grasping the implant from the storage fluid using tweezers, or the like, is simply not practical.

Successful isolation of a corneal implant, or other specimen, generally requires the use of a sieve to separate the implant from the fluid. Isolating the implant in this manner, however, subjects the implant to mechanical forces, which could lead to a loss of the implant. If not damaged, the transparent implant must still be located on the sieve surface and retrieved. The implant must therefore be grasped using tweezers, forceps, or the like. Imparting such force upon the implant, however, can also damage the implant. Using force imparting tools to hold the implant is therefore not desirable. Current isolation techniques are therefore difficult, time-consuming and create additional steps, which can also lead to implant contamination. Thus, it is desired to have an implant storage and handling system, which allows the user to rapidly and successfully retrieve the implant for prompt implantation.

Current devices used to deposit an implant onto the cornea surface generally deposit the corneal implant onto the cornea surface in a bunched or folded conformation. Aligning the implant in planar relation to the cornea surface requires the surgeon to manipulate or tease the implant so as to remove any folds or bends in the implant. Problematically, the step of unfolding the implant on the cornea surface can cause serious trauma to the cornea surface. This trauma can lead to the formation of edema, or other deleterious responses that lead to rejection or displacement of the implant.

Thus, there is believed to be a demonstrated need for a unitary packaging and handling system that provides the desired storage capabilities, easy retrieval of the specimen from that storage, and tools that are operable to retrieve and utilize the specimen without causing damage to the specimen or an implantation site. There is also an additional need for a more effective method for implanting a corneal implant onto a cornea surface.

SUMMARY OF THE INVENTION

The present invention relates to an implant packaging and handling system which includes a storage bottle having an opening to receive a volume of implant storage fluid, and an implant holding tool designed to retain the implant in fluid communication with the implant storage fluid. A storage bottle stopper holds the implant holding tool, so that a portion of the implant holding tool is immersed within the storage fluid upon placement of the stopper into the bottle, placing the implant in fluid communication with the storage fluid. The implant holding tool includes a retaining member detachably mounted to an implant applicator tool. Together they define an enclosure for retaining the implant in a secure, known storage position.

The implant applicator tool has an arcuate-shaped applicator surface with a plurality of openings. The arcuate shaped surface is contoured to correspond to the curvature of the cornea surface, which aids in the proper implantation of the implant to the cornea surface. In one embodiment, the applicator surface has one or more recessed surfaces designed to hold and center the implant on the applicator surface. One or more recessed grooves are also provided to allow fluid to flow between the implant and the applicator surface.

The openings have numerous advantages. The openings provide continuous fluid communication between a retained implant and the implant storage fluid. Upon removal from storage, the openings enable the user to unfold and orient the implant by gently passing fluid through the openings so as to float the implant into a desired central position on the applicator tool surface. Once so positioned, the user is then able to aspirate the fluid/from between the implant and the applicator tool, thereby resting the implant firmly against the applicator tool surface. The applicator tool also includes a central opening providing the user with a reference point for centering the applicator surface, and thus, the implant onto the surface of the cornea.

The present invention also relates to a method of implanting a corneal implant using the implant packaging and handling system. The initial step includes surgically preparing the cornea surface for implantation. Next, the implant and implant holding tool are retrieved from the storage bottle, and the retaining member removed so as to provide an applicator tool together with implant. The applicator can then be attached to a handle for ease of use. The implant is then properly aligned on the applicator tool and deposited onto the surgically prepared cornea surface. Finally, the cornea is restored.

BRIEF DESCRIPTION OF THE DRAWINGS

A better understanding of the invention can be obtained from the detailed description of exemplary embodiments set forth below, when considered in conjunction with the appended drawings, in which.

DETAILED DESCRIPTION OF EXEMPLARY EMBODIMENTS

Figure 1:
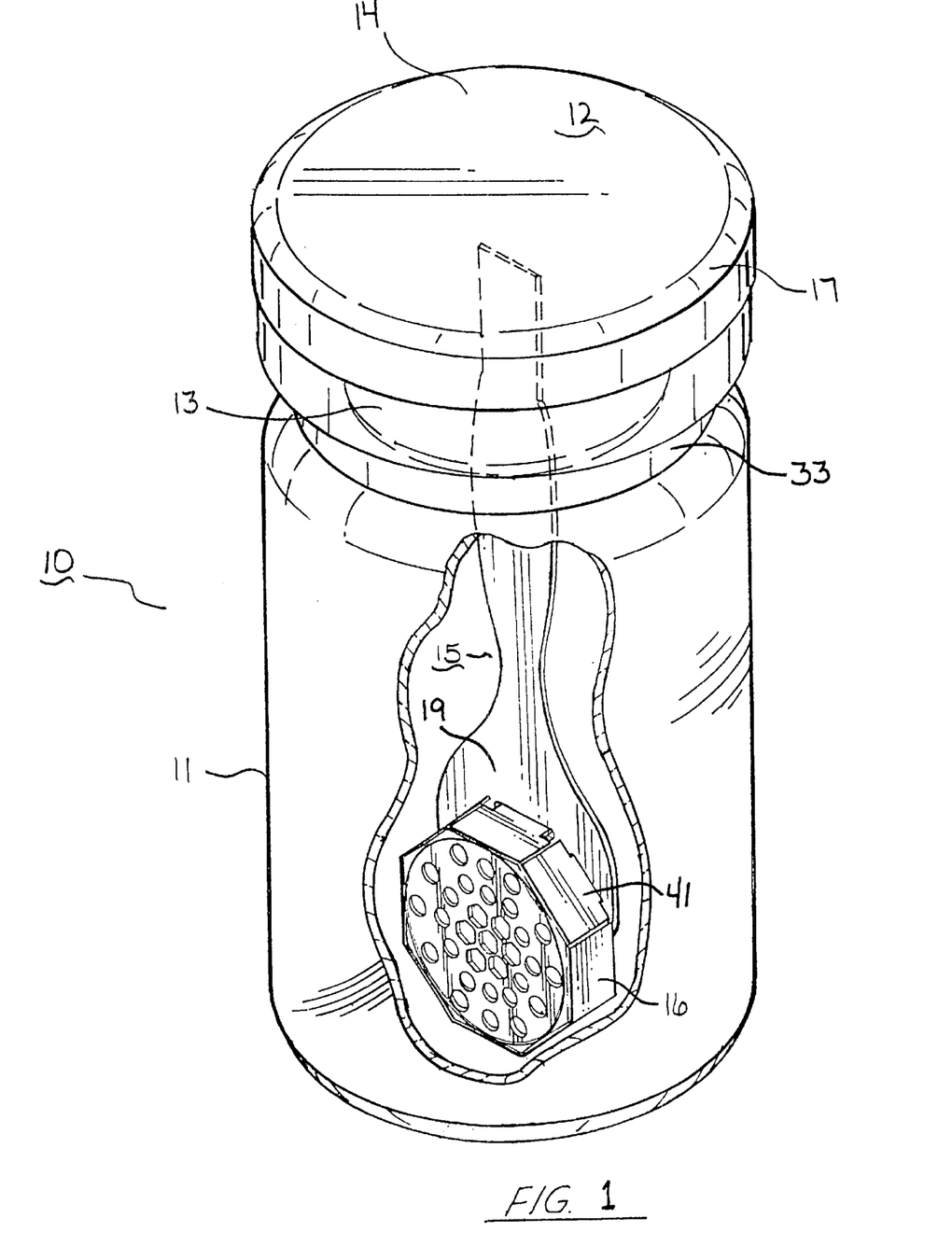
FIG. 1 is a partial sectional view of the implant packaging and handling system of the present invention.

FIGS. 1 through 14 of the drawings show an implant packaging and handling system 10 of the present invention. As illustrated in FIG. 1, the preferred system 10 includes a cylindrical storage bottle 11 for holding implant storage fluid (not indicated). The bottle 11 is sealed by a stopper 12 having an upper cap portion 14 and a plug portion 13, which is adapted to detachably couple to an implant storage tool 15. A protective safety seal 17 provides tamper resistance and maintains the stopper 12 in sealed relation to the bottle 11.

Figures 2, 3, 4:
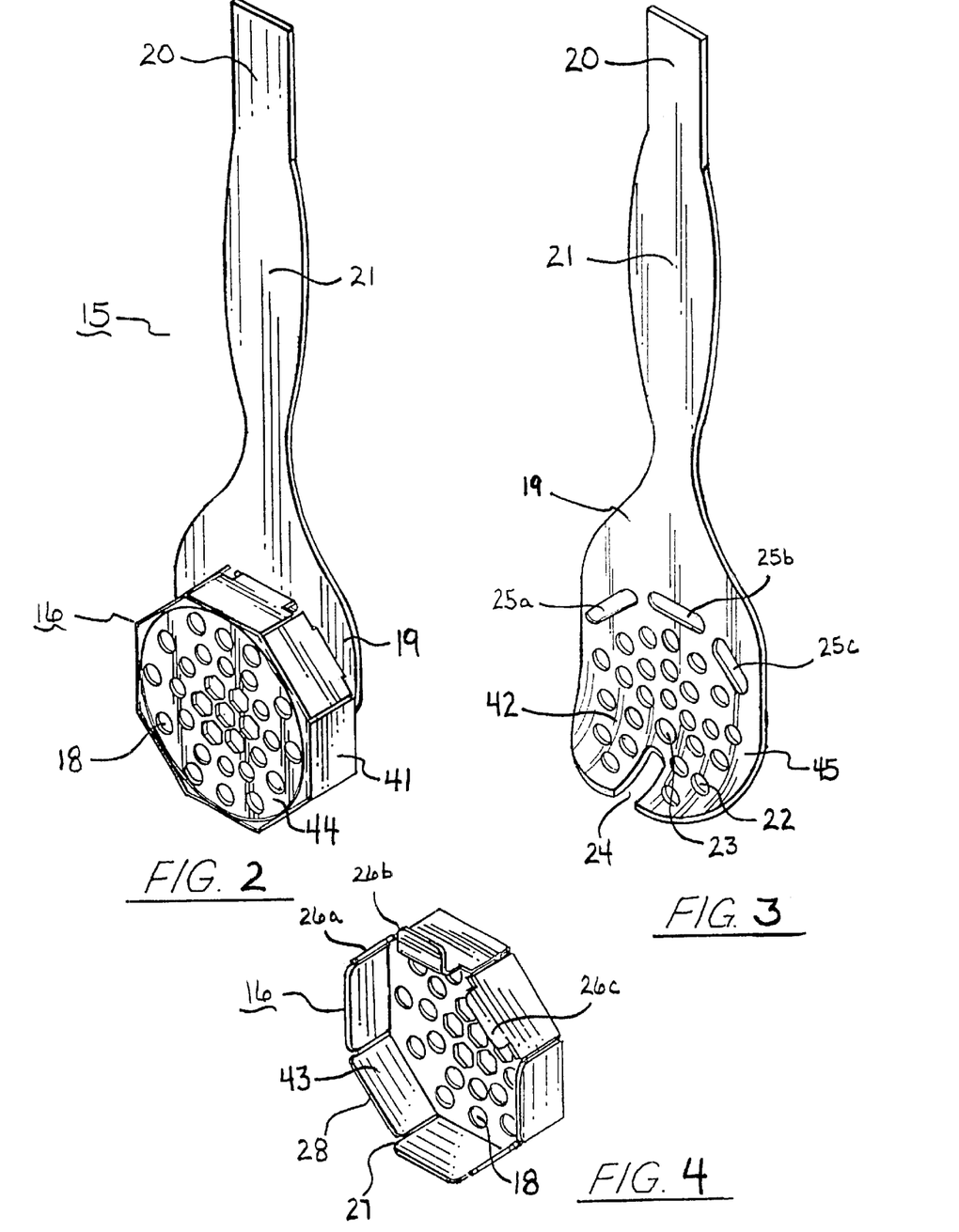
FIG. 2 is a schematic representation of the implant applicator tool fastened to a retaining member, providing the implant storage tool of the present invention.
FIG. 3 is a schematic representation of the implant applicator tool of the present invention.
FIG. 4 is a schematic representation of the retaining member adapted to form an implant retaining enclosure when fastened to the implant applicator tool of FIG. 3.

FIGS. 2 through 4 show a retaining member 16 and implant applicator tool 19, which together define the implant storage tool 15. As illustrated, the retaining member 16 is adapted to detachably engage the implant applicator tool 19, thereby defining an enclosure 41 operable to retain the implant. Both the retaining member 16 and the applicator tool 19 include a plurality of openings 18 and 22, respectively, which allow storage fluid to communicate into the implant retaining enclosure 41. As shown in FIG. 1, the implant retaining enclosure 41 is located on the end of storage tool 15 that is distal to the stopper 12 such that the enclosure 41 is immersed in implant storage fluid when the storage tool 15 is inserted into the bottle 11. When the implant is stored, the enclosure 41 of storage tool 15 holds the implant in the storage fluid, while also providing a user with ready access to the implant. The user simply removes the stopper 12, thereby removing the storage tool 15 from the bottle 11, and detaches the retaining member 16 from the applicator 19 to access the implant.

As illustrated in FIG. 3, applicator tool 19 has a handle attachment arm 20 connected through a body portion 21 to an implant applicator member 45. The body portion 21 is preferably shaped to provide a broad handling surface. For instance, FIGS. 2 and 3 show a body portion 21 having a broad elliptical shape, which allows a user to more easily manipulate the applicator tool 19. As shown, the implant applicator member 45 includes an applicator surface 42 having a plurality of openings 22 to provide fluid communication between the applicator surface 42 and an implant resting thereon. Openings 22 further allow the user to release the implant from the applicator surface 42. More particularly, the user can impart force upon the implant by passing through the opening 22 either a flow of fluid or a cantilever so as to forcibly separate the implant from the applicator member surface 42 (as is shown in FIG. 14).

In a preferred embodiment, the applicator surface 42 has a central opening 23 to help the user align the applicator surface 42 along the visual or optical axis of the eye. As shown, the centrally positioned opening 23 defines a circular opening having a diameter greater than the diameter of the surrounding openings 22. In this way, the user is provided with a central point of reference, which enables the user to align the applicator surface 42 with the optical axis of the eye, and thus, properly position the implant.

Figures 10, 11, 12, 13, 13A:
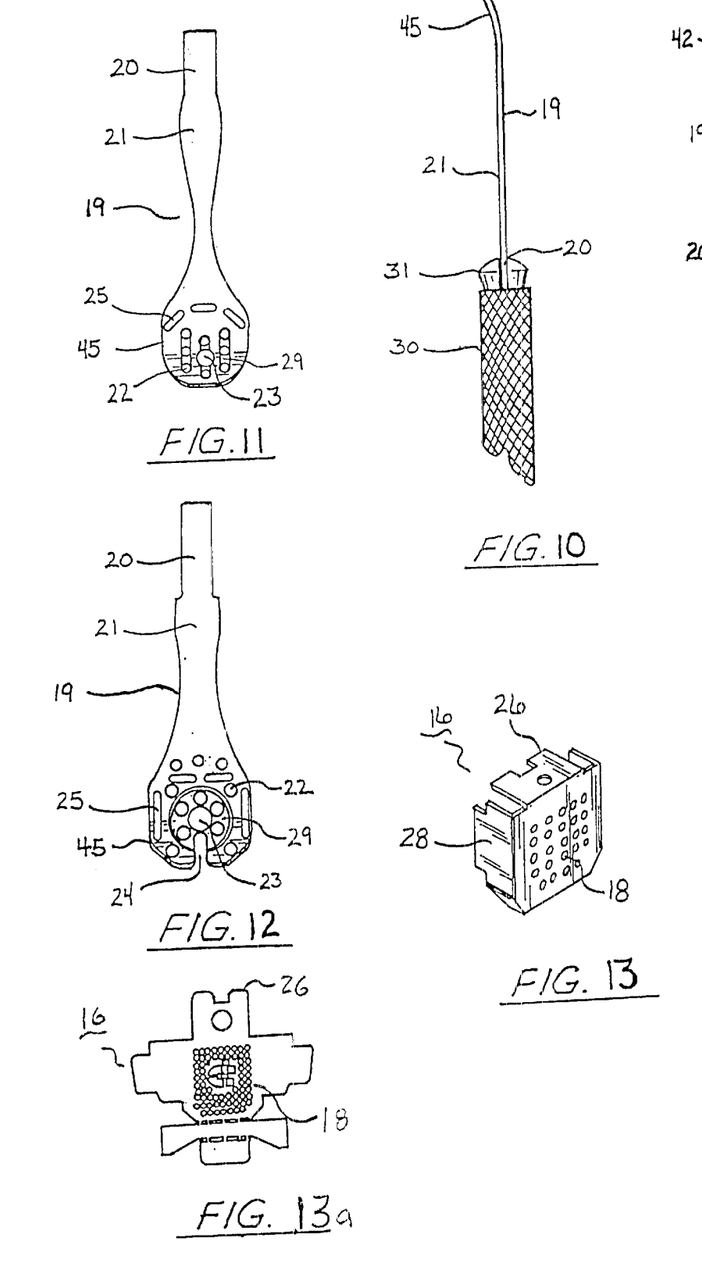
FIG. 10 is a side view of the implant applicator tool secured to a handle, showing the curved surface of the implant applicator tool, which corresponds with the contour of the cornea surface.
FIG. 11 is a schematic representation of an implant applicator tool having a central opening for aligning the applicator tool with the visual or pupillary axis of the eye.
FIG. 12 is a schematic representation of an implant applicator tool having a recessed surface defining a central opening and adjacent alignment slot.
FIG. 13 is a schematic representation of a retaining member adapted to engage with the applicator tools shown in FIGS. 9 and 12.
FIG. 13a is a schematic representation of a retaining member in a flattened form.

In another embodiment, the applicator tool 19 may include an applicator alignment notch 24 positioned integral to the surface 42 of the applicator member 45. For instance, FIGS. 3 and 12 show the notch 24 extending inwardly towards the centrally positioned alignment opening 23. In this embodiment, the notch 24 is used to align the implant on the cornea surface 39, as well as release the implant from the applicator surface 42. Specifically, the notch 24 is dimensioned to allow a cantilever, or like instrument, to pass through the notch, thereby allowing the user to impart force against an implant held on the applicator surface 42. Specifically, the user lifts the application tool 19 away from the cornea surface while simultaneously imparting downward force on the implant through the notch 24 so as to release the implant. One skilled in the art will understand that various notch positionings can be incorporated into the applicator member 45 without departing from the scope of the present invention.

As shown in FIG. 2, the retaining member 16 has an outer surface 44 defining a plurality of openings 18 that provide fluid communication to an implant retained by the enclosure 41. FIG. 4 shows a retaining member 16 disengaged from the applicator tool 19 shown in FIG. 3. To secure the retaining member 16 to the applicator tool 19, the retaining member 16 is provided with attachment tabs 26a–c adapted to insert into corresponding attachment slots 25a–c integral to the applicator tool 19. In use, the retaining member 16 is attached to the applicator tool 19 by simply inserting the tabs 26a–c into the respective corresponding slots 25a–c, and then positioning the bottom surfaces 28 of retaining member side walls 43 against the applicator surface 42. In a preferred embodiment, at least one side wall 43 has an overlapping flexible portion 27 adapted to bend about the distal edge of the applicator surface 42, thereby securely clamping the retaining member 16 to the applicator tool 19. To remove the retaining member 16, the user merely unclamps the flexible portion 27 by bending it away from the applicator tool 19, and lifting the member 16 so as to disengage tabs 26a–c from slots 25a–c.

As illustrated in FIGS. 9, 11, 12 and 13, an alternative attachment tab 26 and attachment slot 25 can also be used with the present invention. For instance, FIG. 12 shows an applicator tool 19 having four separate attachment slots 25, while in comparison FIG. 3 shows an applicator tool 19 having three separate attachment slots 25a–c. It will be understood by those skilled in the art that various embodiments for attachment slots 25 and tabs 26 can be incorporated into the applicator tool 19 and retaining member 16 without deviating from the scope of the present invention.

Figure 5:
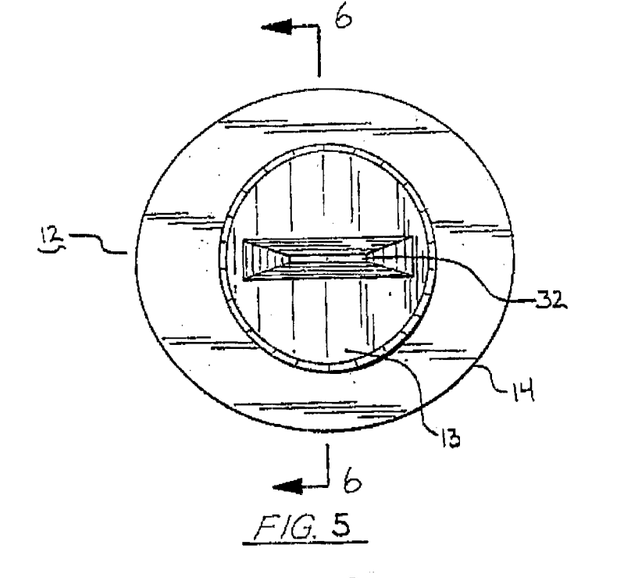
FIG. 5 is a bottom view of a stopper used to seal the storage bottle of the present invention, showing the implant storage tool engagement slot in an open position.
Figure 6:
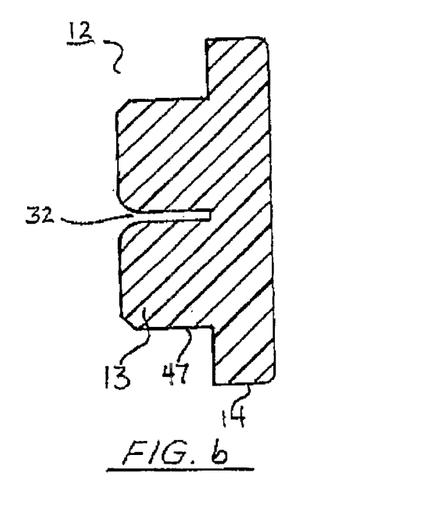
FIG. 6 is a cross-sectional view through the stopper of FIG. 5 taken on line 10—10.
Figure 7:
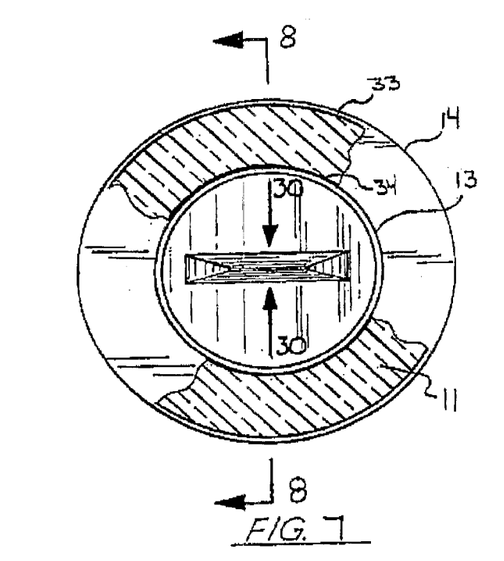
FIG. 7 is a partial sectional view of the bottle stopper positioned within the storage bottle, showing the implant storage tool engagement slot in a closed position.
Figure 8:
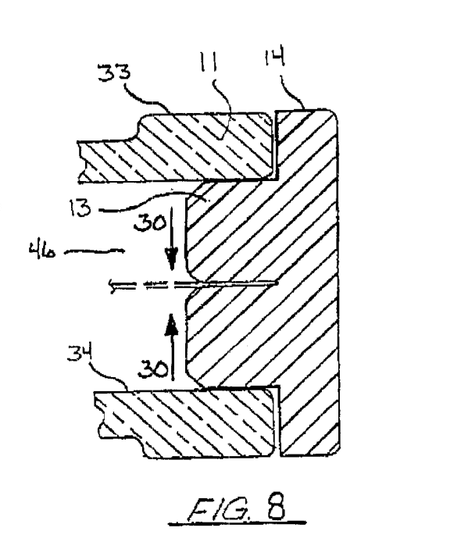
FIG. 8 is a cross-section at view through the stopper and storage bottle of FIG. 7 taken on line 20—20.

As illustrated in FIGS. 5 through 8, a preferred embodiment of system 10 includes a bottle stopper 12 adapted to receive and securely hold the handle attachment arm 20 of the applicator tool 19. The stopper 12 preferably includes an upper cap portion 14 and a plug portion 13 dimensioned to insertably seal the bottle 11. FIG. 5 shows the stopper plug portion 13, which is not inserted into a storage bottle opening 46 (shown in FIG. 8). In comparison to FIG. 5, FIG. 7 shows the plug 13 inserted into the storage bottle opening 46. As illustrated by FIGS. 5 and 7, plug portion 13, when removed from bottle opening 46, adopts an elliptical shape by distending in an outwardly direction along line the 10—10. Likewise, inserting stopper 12 into bottle opening 46 causes the outer diameter of plug portion 13 to conform to the inner diameter of the inner bottle surface 34. In this way, the plug portion 13 becomes inwardly compressed along line 30—30. Referring to FIGS. 6 and 8, cross-section views are shown of stopper plug portion 13 in an out-of-bottle elliptical shape and an in-bottle compressed circular shape, respectively. The utility of this embodiment is described in more detail below.

An engagement slot 32 is located integral to plug portion 13 in an orientation perpendicular to line 10—10. As illustrated in FIGS. 5 through 8, the engagement slot 32 opens or closes in response to either the removal or insertion of the plug portion 13 from the bottle opening 46, respectively. Referring to FIGS. 5 and 6, the engagement slot 32 is shown in an open position. More particularly, when the user removes the stopper 12 from bottle opening 46, the plug portion 13 adopts an unrestrained elliptical shape by distending outwardly along the line 10—10 for opening slot 32. In this way, the engagement arm 20 of the applicator tool 19, which is held by the engagement the slot 32, is easily separated from slot 32 once the stopper 12 is removed from the storage bottle 11. By way of comparison, FIGS. 7 and 8 show the engagement slot 32 adopting a closed conformation upon insertion of the stopper 12 into the bottle opening 46. As shown in FIG. 7, insertion of the stopper 12 into the bottle 11 causes the outer surface 47 of the plug portion 13 to conform to the inner diameter of the bottle opening surface 34, which imparts force in the direction of the line 30—30. In this way, the slot 32 is forced into a tight, closed conformation. Thus, the engagement arm 20 of the applicator tool 19 is held by a slot 32 in a secure position when the stopper 12 is inserted into the bottle 11. The stopper 12 is preferably made of silicone rubber, or other elastomeric material.

Figure 9:
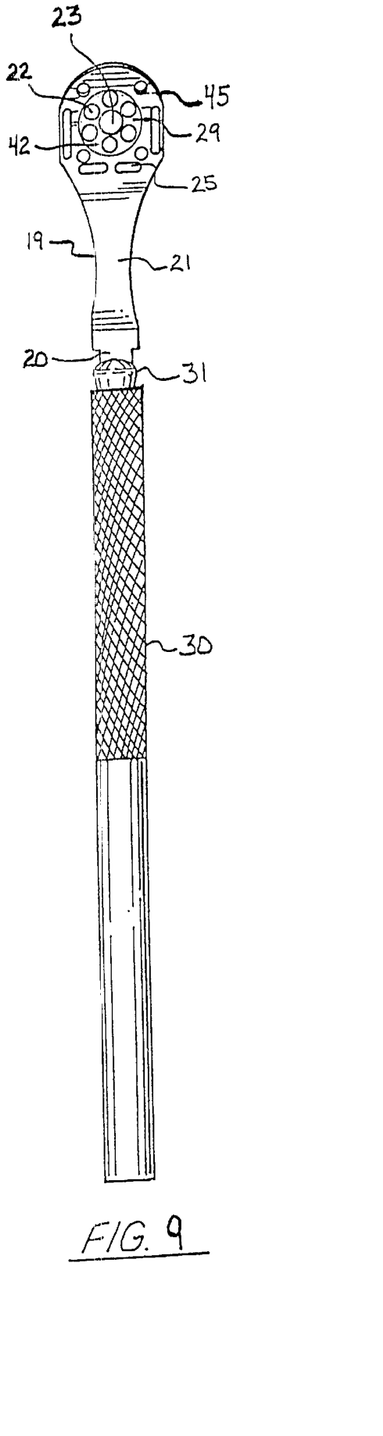
FIG. 9 is a schematic illustration of the implant applicator tool secured to a handle.

FIGS. 9 and 10 show an applicator tool 19 attached to a handle 30. The applicator tool attachment arm 20 detachably mounts to the handle 30 through a handle fastener 31. It will be understood by those skilled in the art that numerous types of handles and handle fasteners are available that can be used with the applicator tool 19 without departing from the scope of the present invention.

As illustrated by FIG. 10, the implant applicator member 45 has a curved applicator surface 42, which corresponds to the curvature of the cornea implant site. This curved surface allows the user to position the curved applicator surface 42 evenly across the cornea surface, enabling the implant to be more evenly deposited onto the cornea surface. Referring to FIGS. 9 and 12, each applicator member 45 is shown having a recessed applicator surface 29. As shown, the recessed surface 29 is preferably circular, thereby allowing a substantially circular implant to be centrally positioned on the applicator member 45. In addition, the central opening 23 which is centered relative to the perimeter of the circular recess 29, provides the user with a reference point for alignment of the applicator member 45 with the pupil diameter. In this way, the implant can be properly aligned on the cornea surface.

FIG. 11 shows an applicator tool 19 having an applicator surface 42 with recessed grooves 29 to allow fluid to flow between the applicator surface 42 and an implant supported on the surface 42. It should be understood by one skilled in the art that alternatively dimensioned recesses and grooves can be formed in the applicator surface 42 without departing from the scope of the present invention. It is advantageous to provide fluid flow between the surface 42 and the implant to enable the user to more easily manipulate the implant while it is on the applicator surface 42. During storage, for example, the implant may come to rest in various folded and bunched conformations. Once the retaining member 16 is removed, the user can manipulate the implant into its desired conformation by gently passing a volume of fluid through the openings 22 and 23. More particularly, the implant will overlap a small volume of fluid, thereby allowing the user to floatingly realign the implant on the applicator surface 42. After the implant is aligned, the fluid can be removed by simply touching the underside of the applicator member 45 with a cotton swab, or like absorbent material.

FIGS. 12 and 13 show an alternative embodiment of an applicator tool 19 and a retaining member 16, respectively. In this embodiment, the retaining member 16 includes four attachment tabs 26 that detachably insert into four corresponding applicator tool attachment slots 25. As shown, the tool 19 and the retaining member 18 include fluid communication openings 22 and 18, respectively. It should be understood that various combinations of tabs, slots, alignment and openings can be incorporated into the tool 19 and the member 16 without deviating from the scope of the present invention.

FIGS. 14a through 14e illustrate the steps of the claimed method of implanting an implant to an exposed surface of the cornea using the system of the present invention. The first step, shown in FIG. 14a, involves the surgical preparation of a portion of the outer surface of the cornea 38 of the eye to form a corneal flap 37, which remains attached to the cornea 38 by way of a hinge 36. This surgical step is commonly known in the art as a lamellar dissectomy, and is typically performed using a keratome (not shown). In a preferred embodiment, the flap is cut deeply enough to dissect the Bowman's membrane portion of the cornea 38. Surgically preparing a corneal flap of 100 to 200 microns, typically 160 to 180 microns, operates to eliminate tension caused by the Bowman's membrane. This step reduces the possibility of implant extrusion due to pressure generated within the cornea 38, which may be caused by the implant. As illustrated, it is preferable to leave the corneal flap 37 attached by way of a hinge 36, thereby allowing the flap 37 to be replaced in the same orientation as before the cut.

Figure 14A:
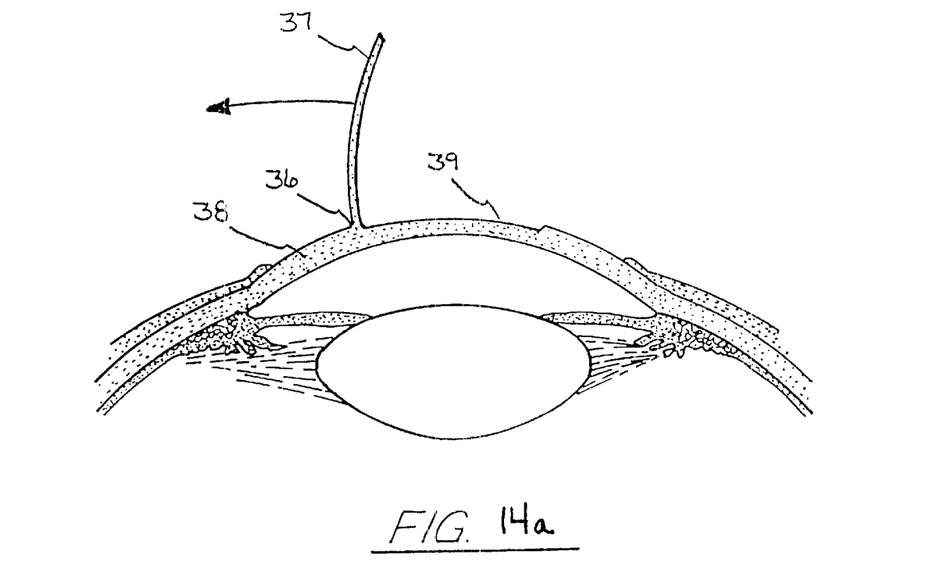
FIGS. 14a, 14b, 14c, 14d and 14e are cross-sectional views of a human eye illustrating the method of introducing an implant to the cornea surface using the implant applicator tool of the present invention.

After the surface 39 is prepared, the surgeon deposits the implant 40 onto the surface 39 using the applicator 19. To retrieve the applicator tool 19, the surgeon first removes the protective seal 17 from around the bottle opening. The implant holding tool 15 is then removed from within the bottle 11 by removing the stopper 12, which holds the storage tool 15. The storage tool 15 is easily separated from the stopper 12 by holding the tool 15 about the body portion 21 and disengaging the tool 15 from the now opened slot 32. Next, the tool arm 20 can be attached to a handle 30, and the retaining member 16 removed. Removing the member 16 presents the implant 40 to the surgeon for implantation. The surgeon is able, therefore, to retrieve an implant 40 from a storage bottle 11 without having to use, at the risk of damaging or losing the implant, a grasping tool, such as tweezers or surgical forceps.

The surgeon then properly aligns the implant 40 on the applicator surface 42 by preferably passing liquid through the openings 22. At this step, the surgeon may gently guide the implant 40 to its proper alignment on the surface 42 using a cannula 35, or other similar device. The implant 40 is positioned on the applicator surface 42 by drawing off the fluid located intermediate to the implant 40 and the applicator surface 42. This can be done by placing a cotton swab, or other absorbent material, against the underside of applicator member 45, which draws off the fluid through openings 22.

Figure 14B:
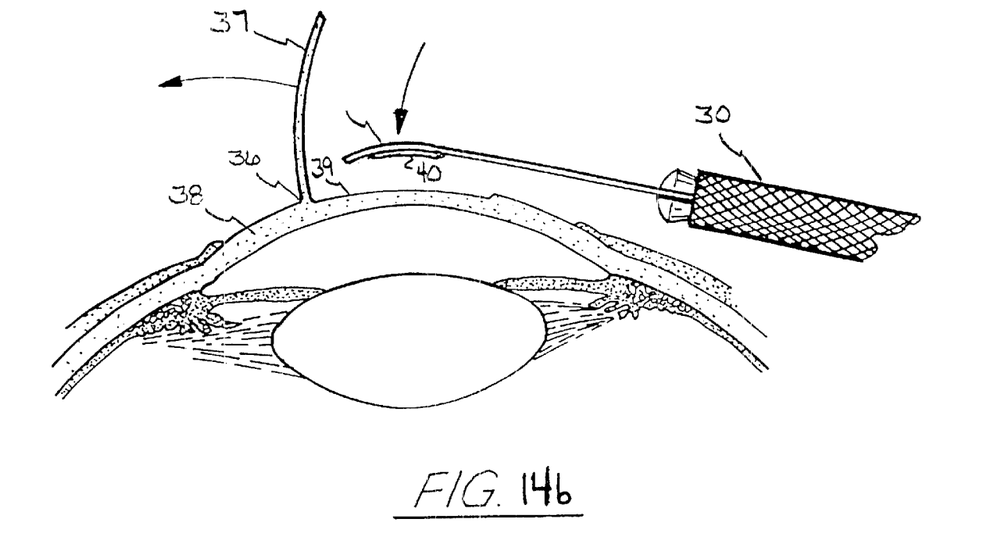
Figure 14C:
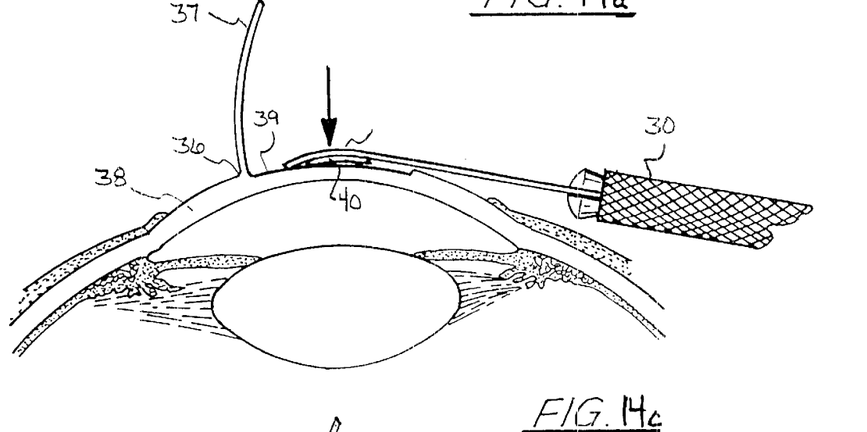

As shown in FIG. 14b, the corneal flap 37 is pulled away from the cornea implantation surface 39. The implant 40 is then positioned over the cornea implantation surface 39 by holding the applicator tool 19 in a generally horizontal position over the surface 39 with the implant 40 facing the surface 39. As shown, the applicator member 45 has an arcuate shaped applicator surface 42, which matches the curved shaped of the cornea surface 39. In this way, as illustrated in FIG. 14c, the applicator member 45 can be evenly placed over the cornea surface 39, reducing trauma to the surface 39. Specifically, the implant 40 is evenly adhered to the surface 39, reducing the need for any manipulation of the implant 40 on the surface 39, which could traumatize the eye as is described above.

Figure 14D:
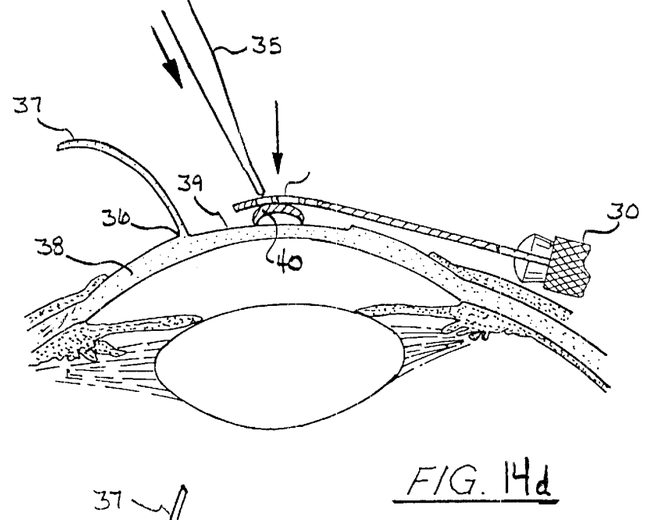
Figure 14E:
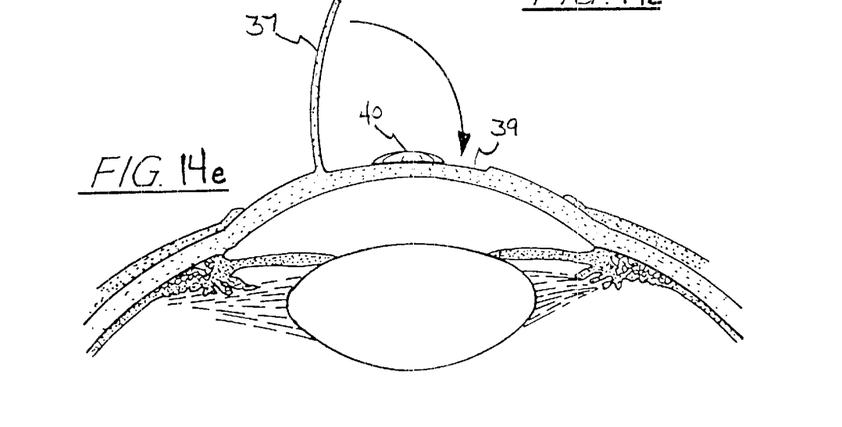

Referring to FIG. 14d, the implant 40 is deposited onto the surface 39 by gently lifting the applicator tool 19 away from the surface 39. As shown, the implant 40 remains adhered to the surface 39. The use of a cannula 35 operable to pass a volume of fluid flow through opening 22, however, can be used to ensure proper deposition of the implant 40 onto surface 39. As shown in FIG. 14e, once the implant is deposited onto the surface 39, the corneal flap 37 is replaced.

Various embodiments of the invention have been described. Nevertheless, it will be understood that various modifications may be made without departing from the spirit and scope of the invention as disclosed and claimed.

I claim:

1. An implant packaging and handling system, comprising:
    (a) a vessel having an opening to receive a volume of storage fluid therein;
    (b) a vessel stop member contoured to seal said vessel opening;
    (c) an implant holder adapted to hold an implant in fluid communication with the storage fluid, said implant holder having a first end detachably connected to said vessel stop member, and a second end distal to said vessel stop member, said second end having a concave surface to hold an implant for application of the implant to an eye.

2. The system claimed in claim 1, wherein said implant holder is detachably connected to said vessel stop member.

3. The system claimed in claim 1, wherein at least a portion of the surface of said implant holder comprises at least one opening.

4. The system claimed in claim 1, further including a locking device adapted to secure said vessel stop member in said vessel opening.

5. The system claimed in claim 1, wherein said implant holder comprises a retaining member detachably mounted to an applicator, wherein said retaining member and applicator define an enclosure adapted to hold the implant.

6. The system claimed in claim 1, wherein said surface is contoured to hold the implant in a substantially planar position.

7. The system claimed in claim 6, wherein at least a portion of said applicator surface is recessed.

8. The system claimed in claim 7, wherein said recessed surface defines a circular recess.

9. The system claimed in claim 8, wherein said circular recess has a perimeter and a central opening centered relative to the perimeter of the circular recess.

10. The system claimed in claim 6, wherein at least a portion of said applicator surface is arcuate shaped.

11. The system claimed in claim 1, wherein said implant holder is adapted to be connected to a handle.

12. An implant packaging and handling system, comprising:
    (a) a vessel having an opening to receive a volume of storage fluid therein;
    (b) a vessel stop member contoured to seal said vessel opening;
    (c) an implant holder comprising an applicator having a first end detachably connected to said vessel stop member, and a second end distal to said vessel stop member said applicator second end adapted to detachably engage a retaining member, said engaged applicator and retaining member defining an enclosure adapted to hold an implant in fluid communication with the storage fluid, said second end having a concave surface to hold an implant for application of the implant to an eye.

13. The system claimed in claim 12, wherein at least a portion of the surface of said implant holder comprises at least one opening, said opening providing fluid communication between the storage fluid and the implant.

14. The system claimed in claim 12, further including a locking device securing said vessel stop member in said vessel opening.

15. The system claimed in claim 12, wherein said applicator first end is adapted to be connected to a handle.

16. An implant packaging and handling system, comprising:
    (a) a vessel having an opening to receive a volume of fluid therein;
    (b) a vessel stop member contoured to seal said vessel opening;
    (c) an implant holder comprising an applicator having a first end detachably connected to said vessel stop member, and a second end distal to said vessel stop member, said applicator second end adapted to detachably engage a retaining member, said engaged applicator and retaining member defining an enclosure adapted to hold an implant;

(d) at least a portion of the surface of said implant holder having a plurality of openings providing fluid communication between the implant and the storage fluid in said vessel; and, (e) a handle, said handle adapted to connect to said first end of said applicator.

17. The system claimed in claim 16, wherein said retaining member has one or more engagement tabs projecting from said retaining member, said applicator having tab engagement slots aligned to receive said retaining member engagement tabs.

18. The system claimed in claim 16, wherein said applicator has a surface contoured to hold the implant in a substantially planar position.

19. The system claimed in claim 18, wherein said applicator surface has a second recessed surface.

20. The system claimed in claim 19, wherein said second recessed surface defines a circular recess having a circumference at least as great as the circumference of a circular implant.

21. An implant packaging and handling system, comprising:

(a) a vessel having an opening to receive a volume of storage fluid therein;

(b) an implant holder adapted to hold an implant in fluid communication with the storage fluid; and (c) a vessel stop member contoured to seal said vessel opening, said vessel stop member operable to detachably secure said implant holder;

wherein said implant holder having a first end detachably connected to said vessel stop member, and a second end distal to said vessel stop member, said second end having a concave surface to hold an implant for application of the implant to an eye.

22. The system claimed in claim 21, wherein said vessel stop member is adapted to change in conformation in response to removal from said vessel opening, wherein said change in shape is operable to release said stop members hold on said implant holder.

23. The system claimed in claim 22, wherein vessel stop member comprises a plug portion defining an integral implant holder engagement slot adapted to receive said implant holder, said engagement slot is operable to hold said implant holder when plug portion is inserted into said vessel opening, and release said implant holder when plug portion is removed from said vessel opening.

* * * * *